United States Patent [19]

Jennings, Jr.

[11] Patent Number: 4,643,200
[45] Date of Patent: Feb. 17, 1987

[54] SAFETY BLOOD DONOR APPARATUS

[76] Inventor: Baldwin P. Jennings, Jr., 330 Sharon La., Staunton, Va. 24401

[21] Appl. No.: 844,889

[22] Filed: Mar. 27, 1986

[51] Int. Cl.⁴ ............................................. A61B 5/14
[52] U.S. Cl. .................................. 128/763; 604/198; 604/184
[58] Field of Search ........ 604/162, 184, 192, 197–198, 604/263, 411–414; 128/763, 766

[56] References Cited

U.S. PATENT DOCUMENTS

| | | | |
|---|---|---|---|
| 3,536,073 | 10/1970 | Farb | 604/162 |
| 3,780,734 | 12/1973 | Wulff | 604/197 |
| 4,257,426 | 3/1981 | Bailey | 604/184 X |
| 4,425,120 | 1/1984 | Sampson et al. | 604/198 |
| 4,573,976 | 3/1986 | Sampson et al. | 604/198 |

Primary Examiner—Dalton L. Truluck
Attorney, Agent, or Firm—B. P. Fishburne, Jr.

[57] ABSTRACT

To replace the customary short flexible tube with attached needle at one end and larger tube connector at its other end, a packaged sterile blood donor assembly is provided. The assembly includes a rigid body having a bore and being equipped at its forward end with a needle and at its rear end with a tube connector having a safety reversible cap. An exterior sleeve on the rigid body is lockable in two positions thereon with the needle in an exposed use position and with the needle retracted and locked in a safety non-use position rearwardly of a safety shield and elastic membrane on the forward end of the exterior sleeve. A discardable needle shield is also provided on the assembly.

3 Claims, 5 Drawing Figures

SAFETY BLOOD DONOR APPARATUS

CROSS-REFERENCE TO RELATED APPLICATION

This application contains common subject matter with application Ser. No. 06/834,573, filed Feb. 28, 1986, for SAFETY BLOOD SAMPLE APPARATUS.

BACKGROUND OF THE INVENTION

1. Field of the Invention

The present invention relates to an improved blood donor apparatus embodying safety features not heretofore known in the prior art.

2. The Prior Art:

The customary blood donor apparatus consists of a short length of small diameter flexible tube equipped at its forward end with a needle having a removable shield and at its rear end with an enlarged tube connector adapted to be coupled to a longer length of flexible tubing leading to a receptor bag for the donated blood. The enlarged tube connector is customarily equipped with a closure cap.

The prior art blood donor apparatus is somewhat deficient in terms of maintaining its sterility and following its use the replacement of the small tubular shield on the needle can easily result in puncturing the skin of personnel handling the discarded equipment, in turn leading to the spread of infectious diseases including AIDS and serum hepatitis.

SUMMARY OF THE INVENTION

The present invention can be summarized as a sterile prepackaged packaged blood donor apparatus or kit including a rigid body having a bore and being equipped at its forward end with a needle and at its rear end with a tube connector having a reversible safety cap. The tube connector is adapted to be coupled with a flexible tube leading to a donated blood receptacle. An exterior sleeve movably mounted on the rigid body is lockable thereon in two positions. In one locked position, the needle is exposed for use, and in the other locked position, the needle is in a retracted safety position rearwardly of a safety shield and membrane on the forward end of the exterior sleeve. The lock for the needle in the safety retracted position is non-releasable. The reversible safety cap is applied to the tube connector in a non-releasable position following use of the apparatus so that it can be discarded in a completely safe non-contaminating condition.

An object of the present invention is to provide a safe non-contaminating blood donor apparatus to replace the customary apparatus of the prior art while providing greatly increased protection against the spread of infectious disease.

A further object of the invention is to provide an improved blood donor apparatus of minute form enabling the entire apparatus to be conveniently taped to the arm of a blood donor in approximately the same space occupied by the prior art device.

A further object of the invention resides in a blood donor apparatus which is practical and economical to manufacture and convenient to use.

Other objects and advantages of the invention will become apparent during the course of the following description.

DETAILED DESCRIPTION

Figures 1, 2, 3, 4, 5:
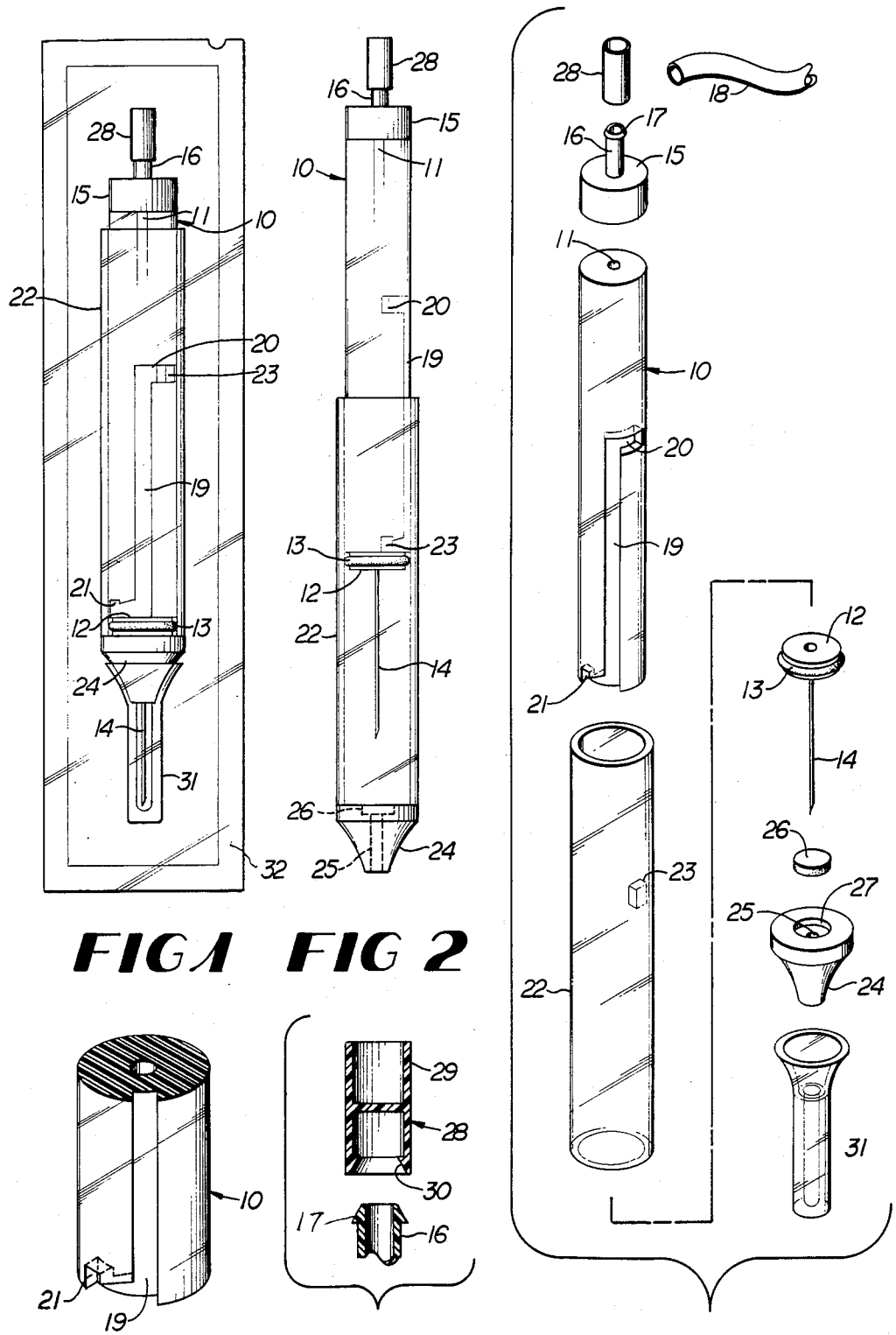
FIG. 1 is a side elevation of a blood donor apparatus according to the present invention in a locked ready for use condition.
FIG. 2 is a side elevation of the apparatus in a retracted and locked safety condition ready for discarding.
FIG. 3 is an exploded perspective view of the apparatus.
FIG. 4 is an enlarged fragmentary perspective view of the body of the apparatus showing a non-releasable locking recess.
FIG. 5 is a central vertical section taken through a safety reversible closure cap.

Referring to the drawings in detail wherein like numerals designate like parts, the numeral 10 designates an elongated rigid cylindrical body having a central longitudinal through bore 11. At its forward end, the body 10 has a needle supporting disc 12 fixed thereto, the disc 12 carrying in an exterior groove an O-ring seal 13, for a purpose to be described. A needle 14 fixed centrally to the disc 12 has its bore in communication with the bore 11 of the rigid body 10 when the disc 12 is assembled with the body 10 in abutting relation with the forward end face thereof.

The rear end of the rigid body 10 has a tube connector 15 suitably fixed thereto and including a short rigid nipple 16 having an end exterior bead 17. The nipple 16 is adapted to be coupled with a suitable length of flexible tubing 18 extending to a receptacle for the donated blood, such as a conventional sterile bag.

The rigid body 10 is provided exteriorly in its side wall with a straight longitudinal groove 19 having a rear end short circumferential locking terminal 20 and a forward end oppositely circumferentially extending stepped non-releasable locking terminal 21. The locking terminal 21 is located at the forward end of the body 10 and the locking terminal 20 is located somewhat rearwardly of the longitudinal center of the body 10.

A straight cylindrical sleeve 22 is engaged movably over the body 10 for limited longitudinal and rotational movement thereon. The sleeve is provided somewhat rearwardly of its longitudinal center with a single internal radially extending locking lug 23 engaged movably in the groove 19 and adapted to travel longitudinally therein and to enter either of the locking terminals 20 or 21 during rotational movement of the sleeve on the body 10.

At its forward end, the sleeve 22 has a tapered safety shield 24 fixed thereto having a central bore 25 formed therethrough to receive the needle 14 coaxially. An elastic membrane 26 is held in a recess 27 of the safety shield 24 at the rear end thereof, and the membrane 26 is also in coaxial alignment with the needle 14.

A reversible safety cap 28 for the tube connector 15 is provided. This cap has a plain cylindrical skirt 29 at one end thereof which can slip over the bead 17 of nipple 16 removably prior to the use of the apparatus in its first locked position shown in FIG. 1. The reversible cap 28 at its other end carries a locking skirt 30 which can be snap locked non-releasably over the bead 17 following the use of the blood donor apparatus after the same is locked in the safety retracted position shown in FIG. 2, and after the tube 18 has been separated from the nipple 16.

A readily removable needle shield 31 is provided as a part of the apparatus which engages frictionally over the safety shield 24 and is readily separable therefrom. The needle shield 31 is discarded after the apparatus is removed from the conventional sterile package 32 ready for use.

In use, the apparatus is removed from the package 32 in a sterile state and with the locking lug 23 engaged in the rear locking terminal 20 of the body 10. The needle 14 is therefore projecting through the membrane 26 and safety shield 24 and forwardly of the safety shield ready for insertion in a vein of a blood donor. The sleeve 22 is now releasably locked in its retracted position on the body 10 substantially at the rear of the shield 24.

The closure cap 28 is removed from the nipple 16, and the nipple is coupled with the flexible tube 18 leading to the blood receptacle. The needle 14 is now inserted into a vein, and the donor's blood flows through the needle, the bore 11, nipple 12 and flexible tube 18 into the blood storage receptacle.

The needle 14 is then withdrawn from the vein of the donor and the sleeve 22 is rotated clockwise on the body 10 to disengage it from the rear locking terminal 20, following which the sleeve is moved forwardly on the body 10 toward the position shown in FIG. 2. At this time, the locking lug 23 advances through the straight groove 19. When the lug 23 contacts the rear of the safety shield 24, the sleeve 22 is again turned clockwise to place the lug 23 in the stepped non-releasable locking terminal 21. At this point, the needle 14 is retracted bodily inside of the sleeve 22 and is disposed rearwardly of the safety shield 24 and its elastic membrane 26. All fluids from the needle are thus captured inside of the sleeve 22 and the apparatus is non-releasably locked in the safety position shown in FIG. 2.

After separation of the flexible tube 18 from the nipple 16, the safety cap 28 is applied to the nipple in the reversed position where its locking skirt 30 interlocks with the bead 17 so that the safety cap cannot be removed. The device is now discarded in the customary manner and it is completely safe against the spread of disease.

The O-ring seal 13 has wiping contact against the bore of sleeve 22 so that no fluid can leak past the seal in either direction. This is an added safety feature against the spread of disease. The drawings show the invention on an exaggerated scale for clarity. In practice, the entire assembly as depicted in FIG. 1 will be approximately the diameter of a common lead pencil and will only be about 1-½ inches in length. Therefore, the device is easily taped to the arm of a donor, as previously explained.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A safety blood donor apparatus comprising
a body having a longitudinal bore,
a needle fixed to one end of the body in communication with said bore and having a rear end disc provided on its periphery with an O-ring seal.
a tube connector fixed to the other end of said body,
a sleeve slidably and rotatably mounted on the exterior of said body and receiving said O-ring wipingly in the interior thereof,
a safety shield having a bore and an elastic membrane fixed to the forward end of said sleeve with the bore of the safety shield and membrane being coaxially aligned with said needle,
interengaging locking means on said body and sleeve whereby the sleeve may be locked to the body in a retracted position with the needle projecting through said membrane and through the bore of the safety shield and forwardly of the safety shield and may be locked to said body in a forwardly extending position with the needle bodily enclosed in said sleeve rearwardly of the safety shield and membrane, and
a closure cap for the tube connector.

2. A safety blood donor apparatus comprising
a body having a longitudinal bore,
a needle fixed to one end of said body in communication with said bore,
a tube connector fixed to the other end of said body,
a sleeve slidably and rotatably mounted on the exterior of said body,
a safety shield having a bore and an elastic membrane fixed to the forward end of said sleeve with the bore of the safety shield and membrane being coaxially aligned with said needle,
interengaging locking means on said body and sleeve whereby the sleeve may be locked to the body in a retracted position with the needle projecting through said membrane and through the bore of the safety shield and forwardly of the safety shield and may be locked to said body in a forwardly extended position with the needle bodily enclosed in said sleeve rearwardly of the safety shield and membrane,
a reversible closure cap for the tube connector adapted to be applied thereto selectively in readily releasable and non-releasable positions, and
said tube connector including a nipple having an enlarged bead and being adapted to be coupled with a flexible tube leading to a receptacle for donated blood, and said reversible closure cap having a plain skirt on one end thereof having a slip fit on said nipple and having a locking skirt at its other end adapted to interlock with said bead in non-releasable manner.

3. A safety blood donor apparatus comprising
a body having a longitudinal bore,
a needle fixed to one end of said body in communication with said bore,
a tube connector fixed to the other end of said body,
a sleeve slidably and rotatably mounted on the exterior of said body,
a safety shield having a bore and an elastic membrane fixed to the forward end of said sleeve with the bore of the safety shield and membrane being coaxially aligned with said needle,
interengaging locking means on said body and sleeve whereby the sleeve may be locked to the body in a retracted position with the needle projecting through said membrane and through the bore of the safety shield and forwardly of the safety shield and may be locked to said body in a forwardly extended position with the needle bodily enclosed in said sleeve rearwardly of the safety shield and membrane,
a reversible closure cap for the tube connector adapted to be applied thereto selectively in readily releasable and non-releasable positions,
a disc secured to the rear end of the needle and abutting the forward end of said body, and
an O-ring seal on and surrounding said disc and wipingly engaging the interior surface of said sleeve.

* * * * *